US008426673B2

(12) United States Patent
Tanahashi et al.

(10) Patent No.: US 8,426,673 B2
(45) Date of Patent: Apr. 23, 2013

(54) PATHOLOGICAL ANIMAL MODEL FOR PELVIC PAIN SYNDROME

(75) Inventors: Masayuki Tanahashi, Tokyo (JP); Katsuro Yoshioka, Tokyo (JP)

(73) Assignee: Astellas Pharma, Inc., Tokyo (JP)

( * ) Notice: Subject to any disclaimer, the term of this patent is extended or adjusted under 35 U.S.C. 154(b) by 394 days.

(21) Appl. No.: 12/811,338

(22) PCT Filed: Jan. 9, 2009

(86) PCT No.: PCT/JP2009/050169
§ 371 (c)(1),
(2), (4) Date: Jun. 30, 2010

(87) PCT Pub. No.: WO2009/088054
PCT Pub. Date: Jul. 16, 2009

(65) Prior Publication Data
US 2010/0313282 A1    Dec. 9, 2010

(30) Foreign Application Priority Data

Jan. 11, 2008   (JP) ................................ P2008-005032

(51) Int. Cl.
*C12N 15/00*   (2006.01)
(52) U.S. Cl.
USPC ............................................................. 800/9
(58) Field of Classification Search ........................ None
See application file for complete search history.

(56) References Cited

U.S. PATENT DOCUMENTS

2007/0253994 A1* 11/2007 Hildebrand .................... 424/422

OTHER PUBLICATIONS

Chuang et al., "Intraprostatic Capsaicin Injection as a Novel Model for Nonbacterial Prostatitis and Effects of Botulinum Toxin A," European Urology, vol. 51, No. 4, pp. 1119-1127, (2007).
Yatkin, "The Soy Effect in the Disease Models of Nonbacterial Prostatitis and Obstructive Voiding," Experimental Biology and Medicine, vol. 232, No. 5, pp. 674-681, (2007).
Sato, "1. Establishment of Experimental Prostatitis Models and Suggestion for Clinic. 2) Experimental Non-Bacterial Prostatitis Model," The Japanese Journal of Urology, vol. 93, No. 2, SS5-2, p. 106, (2002).
Taniguchi et al., "Relation Between the Histological Changes in Young (13 Weeks) Non-Bacterial Prostatitis Model Rats and the Expression of MIC-1 Gene," The Japanese Journal of Urology, vol. 98, No. 2, p. 462, PP-262, (2007).
Abrams et al., "The Standardisation of Terminology in Lower Urinary Tract Function: Report From the Standardisation Sub-Committee of the International Continence Society," Urology, vol. 61, pp. 37-49, (2003).
Fall et al., "EAU Guidelines on Chronic Pelvic Pain," European Urology, vol. 46, pp. 681-689, (2004).
Litwin et al., "The National Institutes of Health Chronic Prostatitis Symptom Index: Development and Validation of a New Outcome Measure," The Journal of Urology, vol. 162, pp. 369-375, (1999).
Niemegeers et al., Suprofen, A Potent Antagonist of Acetic Acid-Induced Writhing in Rats, Arzneimittal-Forschung Drug Research, vol. 25, No. 10, pp. 1505-1509, (1975).
Chuang et al., "Intravesical Botulinum Toxin A Administration Produces Analgesia Against Acetic Acid Induced Bladder Pain Responses in Rats," The Journal of Urology, vol. 172, pp. 1529-1532, (2004).
Boucher et al., "Cyclophosphamide-Induced Cystitis in Freely-Moving Conscious Rats: Behavioral Approach to a New Model of Visceral Pain," The Journal of Urology, vol. 164, pp. 203-208, (2000).
Ghoniem et al., "Irritable Bladder Syndrome in an Animal Model: A Continuous Monitoring Study," Neurourology & Urodynamic, vol. 14, No. 6, pp. 657-665, (1995).
Rudick et al., "Organ Cross Talk Modulates Pelvic Pain," American Journal of Physiology Regulatory Integrative Comparative Physiology, vol. 293, pp. R1191-R1198, (2007).
Vykhovanets et al.; "Expermental Rodent Models of Prostatitis: Limitations and Potential," Prostate Cancer and Prostatic Diseases, vol. 10, pp. 15-29, (2007).
International Search Report from the Japanese Patent Office for International Application No. PCT/JP2009/050169 (Mail date Feb. 24, 2009).

* cited by examiner

*Primary Examiner* — Robert C Hayes
(74) *Attorney, Agent, or Firm* — Finnegan, Henderson, Farabow, Garrett & Dunner, L.L.P.

(57) ABSTRACT

A pathologic animal model characterized in that a pain or discomfort behavior and urinary frequency are induced by administering a stimulative substance into the testes of a small-sized mammal, and a screening method for a therapeutic agent for pelvic pain syndrome, particularly non-bacterial chronic prostatitis, which comprises administering a test substance to the pathologic animal model and measuring pain or discomfort behaviors and/or urinary frequency.

3 Claims, 3 Drawing Sheets

PATHOLOGICAL ANIMAL MODEL FOR PELVIC PAIN SYNDROME

TECHNICAL FIELD

This invention relates to a pathologic animal model which simultaneously develops testicular pain or discomfort behaviors and urinary frequency and a screening method for therapeutic agent for pelvic pain syndrome, particularly non-bacterial chronic prostatitis, by using the pathologic animal model.

BACKGROUND OF THE INVENTION

The pelvic pain syndrome is a general term for pain diseases at the pelvic area and defined by the International Continence Society in 2002 as "the occurrence of persistent or recurrent episodic pelvic pain associated with symptoms suggestive of lower urinary tract, sexual, bowel or gynecological dysfunction, without proven infection or other obvious pathology" (cf. Non-patent Reference 1). The pelvic pain syndrome is classified into urological pain syndrome, gynecological pain syndrome, anorectal pain syndrome, neurological pain syndrome and muscular pain syndrome. The urological pain syndrome is further classified into bladder pain syndrome, urethral pain syndrome, penile pain syndrome, prostate pain syndrome and scrotal pain syndrome (cf. Non-patent Reference 2).

Non-bacterial chronic prostatitis is one of the urological pain syndrome and classified as the category III of the four classifications of prostatitis syndrome proposed in 1999 by National Institute of Health (NIH). The typical symptom of the non-bacterial chronic prostatitis is pain or discomfort at perineal, testicular and penile region and urinary symptoms such as a sensation of incomplete urine emptying and/or urinary frequency. Unlike the case of the acute bacterial prostatitis (category I prostatitis) and chronic bacterial prostatitis (category II prostatitis), a decisive therapeutic method for the non-bacterial chronic prostatitis has not been found because the etiology of the non-bacterial chronic prostatitis has been unclear. In comparison with other lower urinary tract diseases such as benign prostatic hyperplasia, interstitial cystitis and overactive bladder, the non-bacterial chronic prostatitis specifically induces male genital pain including testicular pain which is also mentioned in the chronic prostatitis symptom index of NIH (NIH-CPSI) (e.g., see Non-patent Reference 3).

Intraperitoneal administration of acetic acid-induced pain behavior (writhing) is generally used for evaluating the effect of analgesics (e.g., see Non-patent Reference 4).

Intravesical injection of acetic acid-induced bladder pain in rat (e.g., see Non-patent Reference 5), cyclophosphamide-induced bladder wall lesion resulting in cystitis in rat (e.g., see Non-patent Reference 6), a intravesical injection of acetone-induced irritable bladder dysfunction in *Cercopithecus aethiops* (e.g., see Non-patent Reference 7), a neurogenic cystitis which is induced injection of aujeszky's disease virus (pseudorabies virus) into the abductor caudalis dorsalis muscle in mouse (e.g., see Non-patent Reference 8), and intraprostatic injection of capsaicin-induced inflammation in the prostate gland with pain or discomfort behavior in rat (e.g., see Non-patent Reference 9) have been reported as animal model used for evaluating pain or discomfort derived from lower urinary tract.

On the other hand, it has been reported that hormone, stress, soybean-deficient/excess feeding, mechanical occlusion of the urethra and topical application of ethanol or DNBS into the prostate gland via urethra induced prostatitis in rodents (e.g., see Non-patent Reference 10).

Non-patent Reference 1: Urology, 2003, 61, p 37-49
Non-patent Reference 2: European Urology, 2004, 46, p 681-689
Non-patent Reference 3: Journal of Urology, 1999, 162, p 369-375
Non-patent Reference 4: Arzneimittal-Forschung Drug Research, 1975, 25 (10), p 1505-1509
Non-patent Reference 5: The Journal of Urology, 2004, 172, p 1529-1532
Non-patent Reference 6: The Journal of Urology, 2000, 164, p 203-208
Non-patent Reference 7: Neurourology & Urodynamics, 1995, 14 (6), p 657-665
Non-patent Reference 8: American Journal of Physiology Regulatory Integrative Comparative Physiology, 2007, 293, p 1191-1198
Non-patent Reference 9: European Urology, 2007, 51, p 1119-1127
Non-patent Reference 10: Prostate Cancer and Prostatic Diseases, 10, p 15-29

DISCLOSURE OF THE INVENTION

Problems that the Invention is to Solve

A screening method with using a pathologic animal model which can efficiently evaluate a large number of test substance is essential for production of a therapeutic agent for non-bacterial chronic prostatitis. However, a pathologic animal model which reflects the typical symptoms of non-bacterial chronic prostatitis has not been reported.

Accordingly, the present inventors have carried out extensive studies with the aim of obtaining a pathologic animal model which can be used for evaluation of the effect of test substances on testicular pain or discomfort and urinary frequency which are characteristic symptoms of the non-bacterial chronic prostatitis and of developing a screening method with the animal model.

Means for Solving the Problems

As a result, it was found that a pain or discomfort behavior and changes in urinary function can be induced by an administration of stimulative substances into the testes of an animal.

Thus, the present invention provides:

[1] A pathologic animal model, characterized in that pain or discomfort behaviors and urinary frequency are induced by administering a stimulative substance into the testes of a small-sized mammal.

[2] The pathologic animal model described in [1], wherein the stimulative substance is acetic acid or nerve growth factor (NGF).

[3] The pathologic animal model described in [1], wherein the small-sized mammal is a rodent.

[4] The pathologic animal model described in [3], wherein the rodent is a rat.

[5] A screening method for therapeutic agents for a pelvic pain syndrome, which comprises administering a test substance to the pathologic animal model described in any one of [1] to [4] and measuring pain or discomfort behaviors and/or urinary frequency.

[6] The screening method for therapeutic agents described in [5], wherein the pelvic pain syndrome is urological pain syndrome.

[7] The screening method for therapeutic agents described in [6], wherein the urological pain syndrome is non-bacterial chronic prostatitis.

[8] The screening method described in any of [5] to [7], which comprises administering a test substance before or after administration of a stimulative substance into the testes of the pathologic animal model, and selecting a test substance that improves the pain or discomfort behavior and/or urinary frequency.

Advantage of the Invention

A pathologic animal model in which an administration of stimulative substance into the testes induces pain or discomfort behaviors which can be inhibited by typical analgesics and also evokes urinary frequency without a damage at the bladder is presented in this invention. This animal model is markedly useful as a pathologic animal model for lower urinary tract diseases having pain or discomforts in the urogenital area and urinary frequency, particularly non-bacterial chronic prostatitis.

Thus, candidate substance for the therapeutic agent for non-bacterial chronic prostatitis can be efficiently evaluated by the present invention.

BEST MODE FOR CARRYING OUT THE INVENTION

Figure 1:
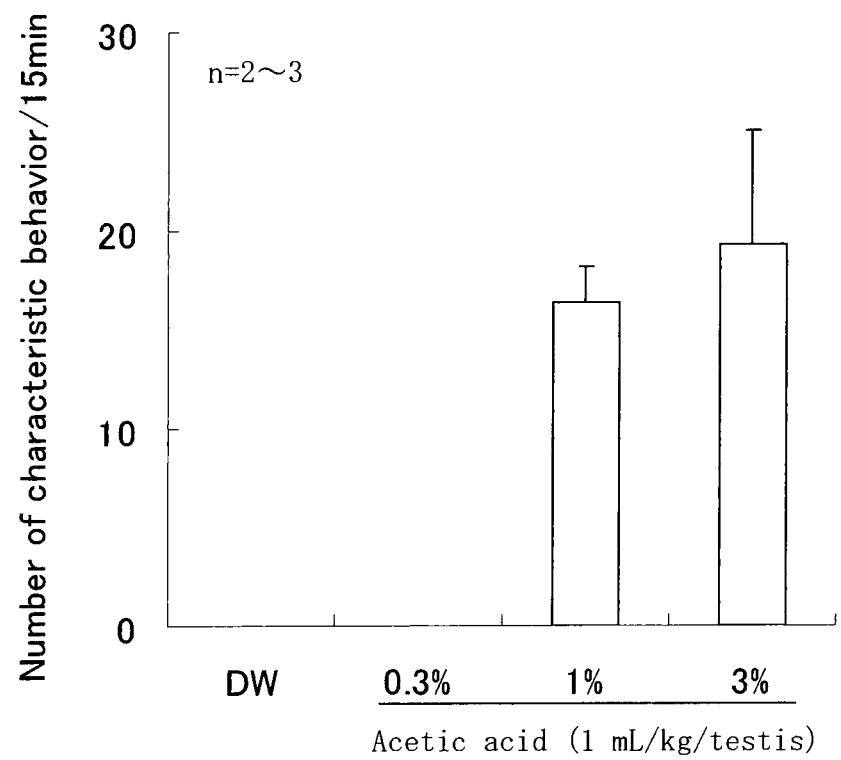
[FIG. 1] A graph showing the number of characteristic pain or discomfort behaviors induced by the intra testicular injection of distilled water or acetic acid aqueous solution in rat.

The following describes the present invention further in detail.

Examples of the small-sized mammal to be used in the present invention include, for example, rodents such as rat, mouse, Mongolian gerbil, rabbit, guinea pig, hamster and the like. With the proviso that the small-sized mammal is male, its age in week, body weight are not particularly limited to so far as it can be applied to the screening of interest.

The stimulative substance to be used in the present invention is a substance which causes pain or discomfort behaviors by administrating it into the body of an animal, and examples thereof include, for example, acetic acid, nerve growth factor (NGF), plasmakinin, serotonin, histamine, acetylcholine, ATP, prostaglandin, arachidonic acid, arachidonic acid metabolite, capsaicin, cytokine, platelet activating factor, active oxygen, nitrogen monoxide (NO), glutamic acid, tachykinin, neurokinin, vasoactive intestinal polypeptide (VIP), pituitary adenylate cyclase activating peptide (PACAP), cholecystokinin, dopamine, noradrenaline, neuropeptide Y, galanin, bombesin, neuromedin, opioid peptide, nociceptin, nocistatin, orexin, cannabinoid, neurotrophic factor, endothelin, vasopressin, hormone, inflammation causing substance, potassium ion, hydrogen ion and chemical substances which directly or indirectly activate or inhibit physiological actions of the above mentioned substances. Dose of the stimulative substance is optionally adjusted in response to the species, body weight and properties of the stimulative substance. For example, in the case of rat, acetic acid may be suitable in a dose of approximately 1 ml/kg as its 0.1% to 10% aqueous solution, and from 0.1 to 1000 µg/ml/kg is suitable for NGF. In general, a stimulative substance is diluted with water, physiological saline or a solvent and administered into testes using a syringe, though not particularly limited to this method.

The pain or discomfort behaviors are characteristic behavior observed in the animal which received the pain or discomfort stimulus, and for example, there may be mentioned behaviors such as 1) stretching its body in a direction parallel to the floor, 2) squashing its lower abdomen against the floor, 3) stretching in a direction vertical to the floor with its arched back, 4) bending the side of its chest with inward moving of the hindlimbs, 5) licking its lower abdominal region including the scrotum, 6) scratching the body with its hindlimbs and 7) biting its hindlimbs. The pain or discomfort behaviors of an animal can be evaluated by measuring frequency or duration of a part or all of the above-mentioned 1) to 7) behaviors within a certain period of time such as from 5 to 25 minutes or from 10 to 30 minutes after the administration of the stimulative substance.

The urinary frequency means increase in number of micturition and is classified into those which are based on polyuria wherein the urine volume becomes large and those which frequently causes the desire for micturition in spite of the normal or less urine volume. These urinary frequency can be evaluated in an animal model by measuring number of micturition, interval time between each micturition, intravesical pressure and bladder capacity. For example, the bladder capacity can be measured as shown in Example 2. In addition to this, the bladder capacity also can be calculated as voided volume per one micturition by continuously measuring actual voided volume and number of micturition in rats.

According to the screening method of the present invention, the test substance may be administered either before or after administration of a stimulative substance, but it is generally administered 5 minutes to 2 hours before the administration of a stimulative substance.

In addition to a conventionally known or novel synthetic compounds, peptides, proteins and the like, for example, tissue extracts, cell culture supernatants and the like of a warm-blooded mammal are used as the test substance. Examples of the conventionally known synthetic compound include, for example, the trkA receptor inhibitors disclosed in WO 01/14380, WO 01/32653, WO 01/78693, WO 02/20479, WO 02/20513, WO 03/027111, JP-A-2003-231687, WO 2005/049033, WO 2005/103010, WO 2005/076695, WO 2007/123269 and the like and the PDE 4 inhibitors disclosed in WO 95/01338, WO 95/24381, WO 01/87281, WO 01/30779, WO 02/102778, WO 96/06843, WO 97/19078, WO 05/49087, JP-A-11-292878, JP-A-11-292877, U.S. Pat. No. 6,544,983 and the like.

Administration of a test substance is carried out by oral administration, intravenous administration, percutaneous administration and the like, in response to the characteristics of each test substance. When a test substance is orally administered, preferred is a method in which it is made into a liquid by dissolving in water or an organic solvent and forcefully administered to an animal using a syringe, a dropping pipette or the like.

In carrying out the screening method of the present invention, it is desirable to set a control group which receive a vehicle solution for a test substance instead of the test substance solution.

EXAMPLES

The following describes the present invention further in detail based on examples, but the present invention is not limited to these examples.

Example 1

1. Intra Testicular Injection of a Stimulative Substance in Rat

Male Wistar rats aged 5 to 12 weeks (Charles River Japan) were used. Positions of the testes were confirmed by keeping the waist of each rat from the dorsal side, and a stimulative substance at a volume of 1 ml/kg was administered into the right and left testes using a syringe equipped with a 27 G needle.

2. Verification of Intra-Testicular Injection

When the intra-testicular administration is achieved, the testes are swelled and become hard in touch. The individuals whose testes were not swelled after the injection were judged as failure in the injection and excluded from further analysis. In addition, dye mixed stimulative substance was injected into the testes and the distribution of the dye within the testes was checked after completion of the experiments to verify whether a stimulative substance was successfully administered or not.

3. Data Analysis

All data was presented as mean and standard error of the mean. The unpaired parametric t-test was used to compare the two group. The parametric Dunnett's multiple comparison test was performed to compare the three groups or more. $P<0.05$ was considered statistically significant.

4. Intra Testicular Injection of Acetic Acid-Induced Characteristic Pain or Discomfort Behavior (1) Dose-dependency of acetic acid: A rat was placed individually in a clear, round, plastic container (Natsume, Japan) for observation immediately after the intra testicular injection of 0.3, 1 and 3% acetic acid aqueous solutions or distilled water. Changes in the behavior of rats were not particularly found in the control group and 0.3% acetic acid intra-testicular administration group. On the other hand, in the 1 and 3% acetic acid treated groups, the following characteristic pain or discomfort behaviors were observed starting 5 minutes after the intra testicular injection: 1) stretching its body in a direction parallel to the floor, 2) squashing its lower abdomen against the floor, 3) stretching in a direction vertical to the floor with its arched back, 4) bending the side of its chest with inward moving of the hindlimbs, 5) licking its lower abdominal region including the scrotum. Among these behaviors, the number of behaviors 1) to 3), frequently observed behavior, was counted from 5 to 20 minutes after the intra testicular injection of acetic acid. No characteristic pain or discomfort behaviors was observed in the rat treated distilled water or 0.3% acetic acid groups. On the other hand, the number of pain or discomfort behaviors in the 1 and 3% acetic acid treated groups were 16±2 times and 19±6 times, respectively (FIG. 1).

Figure 2:
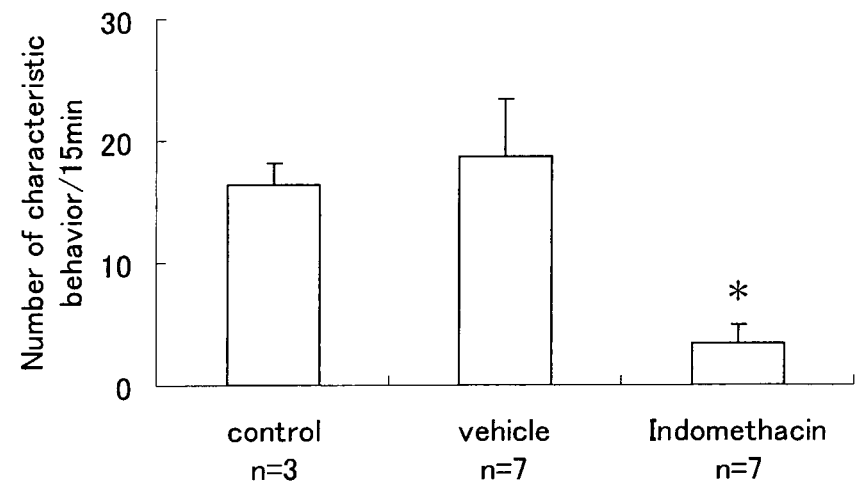
[FIG. 2] A graph showing effects of indomethacin on the number of characteristic pain or discomfort behaviors induced by intra testicular injection of 1% acetic acid in rat. The significant difference was analyzed by t-test, and * represents $p<0.01$.

(2) Effects of indomethacin: Indomethacin at 5 mg/3 mL/kg (Sigma-Aldrich Japan, Japan) or 0.1% $Na_2CO_3$ aqueous solution (vehicle solution) was orally administered 1 hour before the intra testicular injection of 1% acetic acid. Number of the characteristic pain or discomfort behavior was measured in the same manner as described in the above section. Number of the behaviors in vehicle solution treated group was 19±6 times which was not different from that in control group to which nothing was administered before the intra testicular injection of 1% acetic acid. However, the number of the behaviors in indomethacin treated group (3±2 times) was markedly lower than that of the vehicle treated group (FIG. 2).

Figure 3:
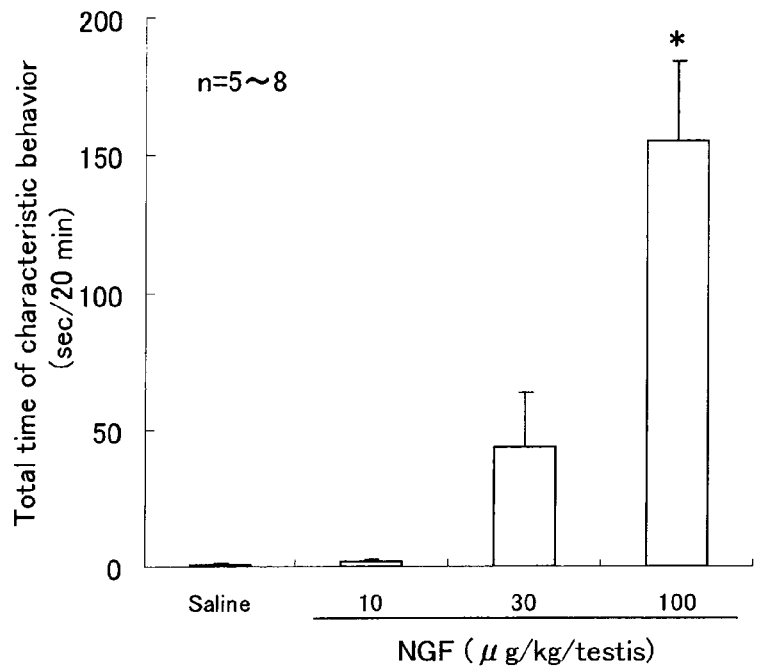
[FIG. 3] A graph showing total time of characteristic pain or discomfort behaviors induced by the intra testicular injection of 100 µg/kg NGF in rat. The significant difference was analyzed by Dunnett's test, and * represents $p<0.01$.

5. Infra Testicular Injection of Rat Nerve Growth Factor (NGF)-Induced Pain or Discomfort Behavior (1) Dose dependency of NGF: Mouse NGF 2.5S (Alomone Labs, Ltd., Israel) at 10, 30 or 100 µg/ml/kg or saline (vehicle solution) was administered to both of the testes in rat. The treated rat was placed in the plastic container and observed. In the 30 and 100 µg/ml/kg NGF treated groups, the following characteristic pain or discomfort behaviors were observed starting from 10 minutes after the intra testicular injection: 1) scratching the body vigorously with hindlimbs, 2) biting tips of the hindlimbs and 3) licking the lower abdominal region including the scrotum. Among these characteristic pain or discomfort behaviors, the behavior of 1) "scratching the body vigorously with hindlimbs" frequently occurred and was observed for a long period of the observation time. Thus, the total time the behavior of 1) was measured by a stopwatch from 10 to 30 minutes after the intra testicular injection. Total time of the characteristic pain or discomfort behavior in the 100 µg/ml/kg NGF treated group (155±29 seconds) was significantly longer than that of the vehicle treated group (1.0±0.4 second) (FIG. 3).

Figure 4:
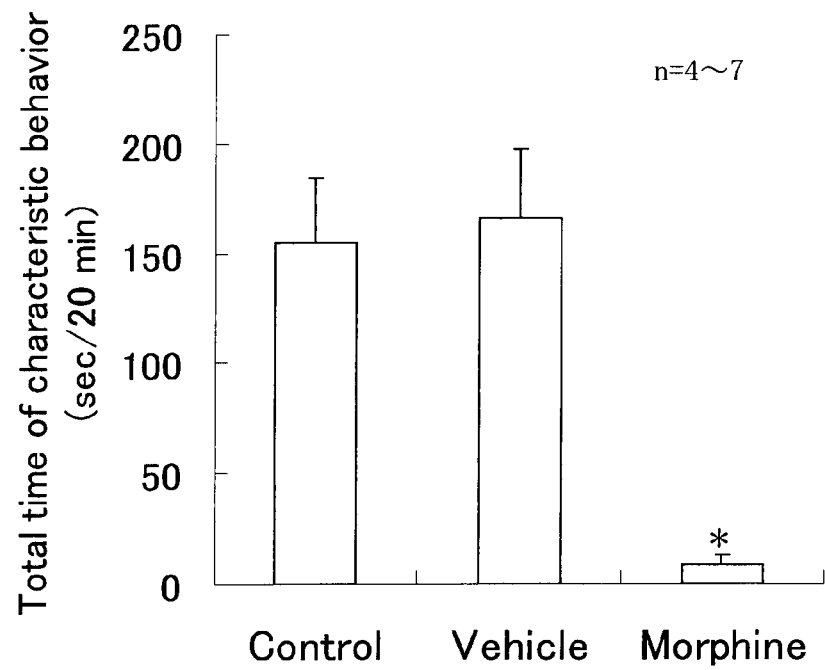
[FIG. 4] A graph showing the effect of morphine on the total time of characteristic pain or discomfort behaviors induced by the intra testicular injection of 100 µg/kg NGF in rat. The significant difference was analyzed by t-test, and * represents $p<0.01$.

(2) Effects of morphine: Morphine (Takeda Chemical Industry, Ltd., Japan) at 5 mg/kg or saline (vehicle solution) was subcutaneously administered 30 minutes before the intra testicular injection of 100 µg/kg NGF. Total time of the above mentioned characteristic pain or discomfort behavior was measured from 10 to 30 minutes after the intra testicular injection of NGF. There is no significant difference in the total time of the behavior between control group, nothing was treated group, and vehicle treated group (167±31 seconds). However, the total time of the behavior in the morphine treated group was markedly and significantly decreased to 9±4 seconds (FIG. 4).

Example 2

1. Measurement of Bladder Function

Male Wistar rats of from 8 to 12 weeks of age (Charles River Japan, Japan) were used. The bladder was exposed through an abdominal midline incision under diethyl ether anesthesia. A PE-50 catheter (Becton Dickinson and Company, Japan) was inserted into the bladder through the bladder dome, and the catheter were sutured at the insertion inlet with a silk thread. The catheter was tunneled subcutaneously at the abdominal cavity and externalized at the back of the neck. After the surgery was finished, the animal was kept in individual cage overnight and used for conscious cystometry in a Bollman cage (KN-326, Natsume, Japan) on the next day. The bladder catheter was connected to a three-way connector which led to an infusion pump (TE-331, TERUMO, Japan)

and a pressure transducer (DX-100, Becton Dickinson and Company, Japan). Physiological saline was continuously infused into the bladder at a rate of 4 ml/h while the intravesical pressure was continuously measured by a pressure amplifier (AP-621 G, Nihon Kohden, Japan) built into a polygraph system (MRP-6008M, Nihon Kohden) and a recorder (LINEARCODER WR 3320, Graphtec Corp, Japan). Bladder capacity was calculated by multiplying the interval time between each micturition by the intravesicla infusion rate of the saline (4 mL/min)

2. Data Analysis

All data was presented as mean and standard error of the mean. The unpaired parametric t-test was used to compare the two group. $P<0.05$ was considered statistically significant.

3. Effects of Intra Testicular Injection of Acetic Acid on Bladder Capacity

Figure 5:
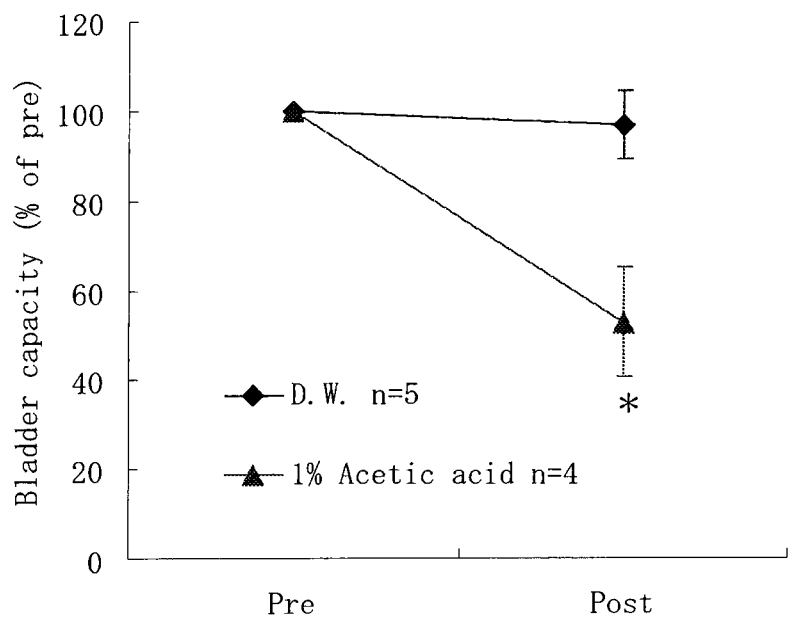
[FIG. 5] A graph showing changes in bladder capacity induced by the intra testicular injection of distilled water or 1% acetic acid in rat. The significant difference was analyzed by the t-test, and * represents $p<0.05$.

The voiding pattern stabilized after cystometry was performed for about 3 h. After that, "pre bladder capacity" was recorded for 1 hr. Immediately after the last void during the control period, the rat was removed from the cage. Distilled water (1 ml/kg) or 1% acetic acid (1 ml/kg) were injected into the testes. Immediately after the injection, each rat was placed back in the Bollman cage and cystometry was restarted. Bladder capacity was measured from 30 to 60 min after the intra testicular injection, and expressed as a percent of the pre bladder capacity. Changes in the bladder capacity in the distilled water treated group was $97\pm8\%$, thus showing no significant change. On the other hand, the bladder capacity was markedly lowered to $53\pm12\%$ by the intra-testicular injection of 1% acetic acid aqueous solution. This change was significant in comparison with that of distilled water treated group (FIG. 5).

4. Effects of Intra Testicular Injection of NGF on Bladder Capacity

Figure 6:
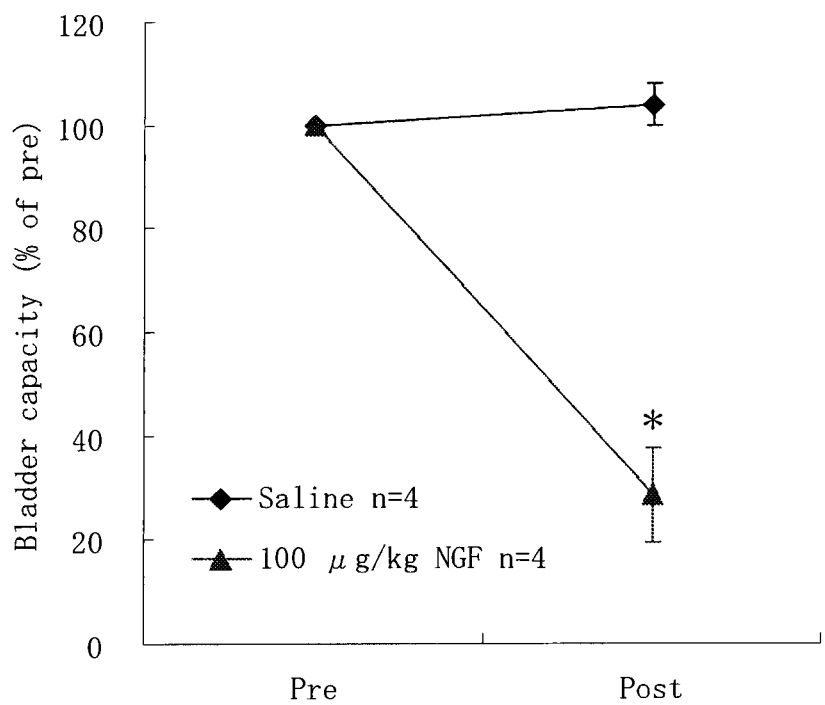
[FIG. 6] A graph showing changes in bladder capacity induced by the intra testicular injection of physiological saline or 100 µg/kg NGF in rat. The significant difference was analyzed by t-test, and * represents $p<0.01$.

The voiding pattern stabilized after cystometry was performed for about 3 h. After that, "pre bladder capacity" was recorded for 1 hr. Immediately after the last void during the control period, the rat was removed from the cage. Physiological saline (1 ml/kg) or 100 μg/kg NGF (1 ml/kg) were injected into the testes. Immediately after the injection, each rat was placed back in the Bollman cage and cystometry was restarted. Bladder capacity was measured from 30 to 60 min after the intra testicular injection, and expressed as a percent of the pre bladder capacity. The bladder capacity in the saline treated group was $104\pm14\%$, thus showing no significant change. On the other hand, the bladder capacity was markedly lowered to $29\pm9\%$ by the intra-testicular injection of 100 μg/kg NGF. This change was significant in comparison with that of physiological saline treated group (FIG. 6).

Example 3

Screening Using Intra Testicular Injection of Acetic Acid in Rat

1. Pain Behavior Study

The number of characteristic pain or discomfort behaviors in a rat treated acetic acid into the testes was measured in the same manner as in Example 1. From 1 to 100 mg/kg of a test substance was dissolved or suspended in 0.5% methylcellulose aqueous solution in a liquid volume of from 3 to 5 ml/kg and orally administered 15 to 60 minutes before the testicular injection of 1% acetic acid, and the number of the characteristic behaviors was measured from 5 to 20 minutes after the intra testicular injection.

2. Bladder Function Study

Change in the bladder function in a rat treated acetic acid into the testes was measured in the same manner as in Example 2. From 1 to 100 mg/kg of a test substance was dissolved or suspended in 0.5% methylcellulose aqueous solution in a liquid volume of from 3 to 5 ml/kg and orally administered 15 to 60 minutes before the testicular injection of 1% acetic acid. Pre bladder capacity was measured for 1 hour before the intra testicular injection. The bladder capacity was measured from 30 to 60 minutes after the intra testicular injection. Changes in bladder capacity was calculated as a percent of the pre bladder capacity 3. Selection of Test Substance A test substance which significantly suppressed one or both of the number of the characteristic pain or discomfort behavior and changes in bladder capacity better than 0.5% methylcellulose aqueous solution (vehicle solution) is selected as a candidate substance for therapeutic agents for non-bacterial chronic prostatitis.

INDUSTRIAL APPLICABILITY

A pathologic animal model of the present invention simultaneously developing a testicular pain or discomfort behaviors and urinary frequency is markedly useful as an animal model which reflects the symptoms of pelvic pain syndrome, particularly non-bacterial chronic prostatitis. The screening method using this animal model can efficiently evaluate a candidate substance for therapeutic agent for pelvic pain syndrome, particularly non-bacterial chronic prostatitis.

The invention claimed is:

1. A pathological animal model for pelvic pain syndrome induced by administering acetic acid or nerve growth factor (NGF) into the testes of a small-sized mammal.

2. The pathologic animal model described in claim 1, wherein the small-sized mammal is a rodent.

3. The pathologic animal model described in claim 2, wherein the rodent is a rat.

* * * * *